United States Patent [19]

Varadaraj et al.

[11] Patent Number: 5,811,290
[45] Date of Patent: Sep. 22, 1998

[54] BIOREMEDIATION METHOD OF HYDROCARBON CONTAMINATED SOILS, WATER, AND/OR SLUDGE USING UREA-SURFACTANT CLATHRATES

[75] Inventors: Ramesh Varadaraj, Flemington; Cornelius Hendrick Brons, Washington, both of N.J.

[73] Assignee: Exxon Research and Engineering Company, Florham Park, N.J.

[21] Appl. No.: 946,422

[22] Filed: Oct. 7, 1997

Related U.S. Application Data

[62] Division of Ser. No. 300,006, Sep. 2, 1994, Pat. No. 5,705, 690.

[51] Int. Cl.⁶ .......................... A61K 33/42; A01N 59/26; B09B 3/00; C07C 211/00
[52] U.S. Cl. ....................... 435/262.5; 210/600; 424/601; 564/1.5; 510/108; 510/535
[58] Field of Search ................... 210/600; 435/262.5; 510/108, 5, 35; 564/1.5; 252/DIG. 1, 6, 11; 424/601

[56] References Cited

U.S. PATENT DOCUMENTS

| | | | |
|---|---|---|---|
| 4,265,779 | 5/1981 | Gandolfo et al. | 252/135 |
| 4,529,534 | 7/1985 | Richardson | 252/100 |
| 4,624,713 | 11/1986 | Morganson et al. | 134/252 |
| 4,704,233 | 11/1987 | Hartman et al. | 252/527 |
| 4,861,502 | 8/1989 | Caswell | 252/8.75 |
| 5,474,698 | 12/1995 | Rolando et al. | 252/90 |
| 5,575,893 | 11/1996 | Khan et al. | 162/199 |

FOREIGN PATENT DOCUMENTS 748877  5/1956  United Kingdom.

OTHER PUBLICATIONS

McAdie, Canadian J. of Chem., vol. 40. 2195–2203, 1962.
Chenite; et al Macromolecules, 25, 776–782, 1992.
Chenite, et al Macromolecules, 24, 2221–2225, 1991.
Casal, et al, J. Chem. Phys., 80, 1407–1401, 1984.

*Primary Examiner*—David M. Naff
*Assistant Examiner*—Deborah K. Ware
*Attorney, Agent, or Firm*—Gerard J. Hughes

[57] ABSTRACT

A method and composition for enhancing the biodegradation of hydrocarbon contaminated soil, water, and/or sludge are disclosed. The composition comprises an adduct of urea with a non-ionic surfactant and a phosphorous source. The disclosed method provides for the application of a degradation effective amount of a composition which comprises a N:P ratio which ranges from 10:2 to about 10:0.5 and the urea and non-ionic surfactant are present in the adduct in a weight ratio ranging from 98:2 to 75:25. Further, the method of biodegradation is carried out by the application of the composition to provide for a C:N:P ratio of 100:10:1 to 100:1:001. The C:N:P ratio is based on the weight percent of the hydrocarbon contaminate in the soil, water and/or sludge sites to be treated. Surfactants which are useful in the disclosed composition and method have from about 2 to fifty ethylene oxide groups; and comprise such compounds as alkylethoxylates, alkyl ethoxylated phosphates, alkyl ethoxylated amines, alkylethoxylated ammonium salts, etc.

4 Claims, No Drawings

BIOREMEDIATION METHOD OF HYDROCARBON CONTAMINATED SOILS, WATER, AND/OR SLUDGE USING UREA-SURFACTANT CLATHRATES

This is a division, of application Ser. No. 300,006, filed Sep. 2, 1994, now U.S. Pat. No. 5,705,690.

FIELD OF THE INVENTION

This invention relates to urea-surfactant clathrates and their use in enhancing the microbial degradation of hydrocarbon contaminated soils and water.

BACKGROUND OF THE INVENTION

As is well-known there are several microbial species found in soil and water that are capable of assimilating petroleum hydrocarbons. Unfortunately, the rate of microbial assimilation of petroleum hydrocarbons is relatively slow. It is necessary therefore to stimulate the microbial assimilation of petroleum hydrocarbons if bioremediation is to be utilized in removing such pollutants from soils and water.

In general, the rate and extent of microbial utilization of petroleum hydrocarbons is limited by the concentration of microbial nutrients and microflora available at the hydrocarbon water interface. Therefore, microbial nutrients, especially nitrogen containing nutrients like urea, have been added to contaminated soil or water as a method for enhancing the biodegradation of the petroleum contaminants. Because these nitrogen containing microbial nutrients are generally water soluble, and because the petroleum hydrocarbons are hydrophobic several different techniques have been used for delivering the nutrients to the hydrocarbon-water interface. For example, one technique employed is to coat the nutrients with a material such as petrolatum in an attempt to keep the nutrient at the hydrocarbon water interface. Another technique that has been employed is to deliver the nutrients in an aqueous solution along with a surfactant which aids in delivering the microbial nutrients to the hydrocarbon-water interface.

There are, of course, many other facets to the treatment of contaminated soils and water and many researchers have worked toward discovering more successful processes for improving biodegradation of contaminated soils and water.

It is the object of the present invention to provide novel compounds that have particular utility in enhancing microbial degradation of hydrocarbon contaminated soils and water.

It is another object of the present invention to provide compositions containing such novel compounds suitable for use in stimulating the propagation of naturally occurring, hydrocarbon assimilating, microflora to enhance the bioremedation of hydrocarbon contaminated soils and water.

SUMMARY OF THE INVENTION

Simply stated, one embodiment of the present invention provides novel compounds comprising an adduct of urea with a non-ionic surfactant.

In another embodiment of the present invention, there is provided a composition suitable for enhancing the bioremediation of contaminated soils and water which comprises at least one adduct of urea with a non-ionic surfactant, preferably in combination with a phosphorous source.

These and other embodiments of the present invention will become more apparent upon reading the detailed description which follows.

DETAILED DESCRIPTION OF THE INVENTION

Novel compounds of the present invention are adducts or inclusion complexes of urea with a non-ionic surfactant, in which urea is the "host" and the surfactant is the "guest". In general, weight ratio of urea to surfactant in the adduct will be in the range from about 98:2 to about 75:25, and preferably in the range from about 80:20 to about 76:14.

The non-ionic surfactant suitable in forming the novel compounds of the present invention are those surfactants which are capable of forming clathrates with urea. Non-limiting examples of such non-ionic surfactants are alkyl ethoxylated phosphates, alkyl ethoxylated-amines, alkyl ethoxylated ammonium salts, alkyl ethoxylated sugars and alkyl ethoxylated polyhydric alcohols and their cyclic ethers, such as sorbitol and sorbitan, in which the alkyl groups will have from about 8 to about 22 carbon atoms and in which the ethylene oxide groups will range from about 2 to 50 and may be monodispersed or polydispersed.

The adducts of the present invention can be readily synthesized by co-crystallizing urea and the surfactant from an appropriate solvent. Typical solvents in the preparing the urea-surfactant adducts include alcohols such as methanol and mixed solvents such as methanol/isopropyl alcohol in volume ratios of about 80 to 20. Typically, the urea and surfactant are dissolved in the solvent at elevated temperatures, e.g., at about 50° C., and thereafter the solvent is allowed to evaporate slowly with the concommittant formation of crystals of the adduct.

Not wishing to be bound by any theory or mechanism it is believed that the novel surfactant urea adducts of the present invention when contacted with water disassociate in such a fashion that at least some of the urea molecules stay associated with the head group of the surfactant thereby enhancing the delivery of the urea to the hydrocarbon-water interface where it is most needed for stimulating microbial growth and assimilation of hydrocarbon contaminants.

In any event, compositions for enhancing the biodegradation of hydrocarbon contaminated soils and water comprise at least one adduct of urea and a non-ionic surfactant. Preferably, the surfactant will be selected from those surfactants described above. Preferably the urea-surfactant adduct is combined with a phosphorous source. It is particularly preferred, however, that the urea surfactant clathrate be combined with the phosphorus source or other microbial nutrients to obtain a composition having a N:P ratio in the range of about 10:2 to about 10:0.5 and preferably about in the range 10:1. Such other microbial nutrients that can be added to the clathrate include ammonium hydrogen phosphate, sodium phosphate, and the like. In some instances, more than one adduct of urea and non-ionic surfactant can be successfully combined.

In addition to the urea surfactant adduct and phosphorous source, optionally, the compositions may include other components such a salicylates to stimulate aromatic degradation and micro nutrients typically used in bioremediation processes.

Non-limiting examples of various compositions are given in Table 1 which follows.

TABLE 1

| Formulation | Urea Surfactant/Wt. % | Phosphorous Source/Wt. % |
|---|---|---|
| 1 | Urea-Oleyl-2-ethyoxylate/44% Urea-trilaurethphosphate/44% | $NH_4H_2PO_4$/12% |
| 2 | Urea-tetradecylammonium salicylate/44% Urea-trilaurephosphate/44% | $NH_4H_2PO_4$/12% |
| 3 | Urea-trilaureth phosphate/83.4% | $NH_4H_2PO_4$/10.6% Sodium Salicylate/6% |

In treating contaminated soil and water in accordance with a the present invention, the urea surfactant composition is applied to the soil or water by broadcasting in an amount sufficient to enhance the rate of biodegradation of the contaminated soil and water. The amount applied can vary broadly and typically will depend upon the weight percent of hydrocarbon contaminant on the soil or water. Preferrably, the amount of the urea-surfactant formulation will be applied in an mount sufficient to provide a C:N:P ratio of from about 100:10:1 to about 100:1:0.1.

When treating contaminated soil with compositions of the present invention, it is generally preferred or attempt to maintain the moisture content of the hydrocarbon contaminated soil at from about 10 wt. % to 35 wt. %.

The following examples will more fully illustrate the invention.

EXAMPLES 1–10

These examples demonstrate the preparation of the novel urea non-ionic surfactant adducts of the present invention.

To 20 gm. of methanol was added 5 gm. of urea and 1 gm. of the surfactant shown in Table 2. The mixture was heated until the urea and surfactant both dissolved. After cooling to room temperature, the solvent was allowed to evaporate very slowly and the urea-surfactant clathrate crystals formed were separated by filtration, washed with cold methanol and dried. The weight ratio of urea to surfactant for each composition prepared is given in Table 2.

which had approximately one weight percent contaminant as determined by EPA Method 418.1. To three separate polypropylene pans, 12 inches long, by 8 inches wide and 3 inches deep, 2,000 gms of the hydrocarbon contained contaminated soil were added. Two of the pans were treated by uniformly broadcasting the urea-surfactant formulation onto the soil surface to provide a C:N:P of 100:10:1. The soil in the pans were watered and hand-tilled weekly. The amount of water applied was sufficient to provide a moisture content of about 17 wt. %. After 8 weeks, the percent petroleum hydrocarbon biodegraded was determined for each of the samples using the EPA Method 418.1 with the following modifications.

1) The soil sample size was increased to 30 grams.
2) The acidification step specified in the test was eliminated.
3) The drying agent used was magnesium sulfate.
4) The amount of drying agent required by the test was increased to assure effective drying.
5) A four hour time period for soxhlet extraction was employed.
6) The amount of silica gel used in the final filtration step was increased.

The microbial population was determined on the soil samples 2 weeks after treatment. The standard most probable number (MPN) microbioloy method was employed and

TABLE 2

| Example | Surfactant Commercial Name | Nominal Formula | Wt. % Urea/ Surfactant |
|---|---|---|---|
| 1 | Neodol 91-8[1] | $C_{10}H_{21}-(OCH_2CH_2)_8-OH$ | 83/17 |
| 2 | Neodol 91-8[1] | $C_{10}H_{21}-(OCH_2CH_2)_8-OH$ | 90/10 |
| 3 | Neodol 91-8[1] | $C_{10}H_{21}-(OCH_2CH_2)_8-OH$ | 95/5 |
| 4 | Brij-92[2] | $C_{18}H_{35}-(OCH_2CH_2)_2-OH$ | 83/17 |
| 5 | Trilaureth Phosphate | $(C_{12}H_{25}-(O-CH_2CH_2)_4-O)_3-P=O$ | 83/17 |
| 6 | Tween-80[3] | $C_{18}H_{35}-CO_2\text{-Sorbitan-}(OCH_2CH_2)_{10}-OH$ | 83/17 |
| 7 | Span-80[4] | $C_{18}H_{35}-CO_2\text{-Sorbitan}$ | 83/17 |
| 8 | Span-20[4] | $C_{12}H_{25}-CO_2\text{-Sorbitan}$ | 83/17 |
| 9 | E-14-5 Ethoxylated Amine[5] | $C_{11}H_{23}-O-(CH_2)_3-N\big<{{(OCH_2CH_2)_y-OH}\atop{(OCH_2CH_2)_x-OH}}$, $x+y=5$ | 83/17 |
| 10 | E-14-5 Ethoxylated Ammonium Salicylate | $C_{11}H_{23}-O-(CH_2)_3-N\text{-Salicylic Acid}\big<{{(OCH_2CH_2)_y-OH}\atop{(OCH_2CH_2)_x-OH}}$, $x+y=5$ | 83/17 |

[1]Neodol 91-8 is the tradename for an ethoxylated alcohol sold by Shell Chemical Company, Houston, TX.
[2]Brij-92 is the tradename for an ethoxylated alcohol sold by ICI America's, Inc., Wilmington, DE.
[3]Tween-80 is the tradename of an ethoxylated Sorbitan ester sold by ICI American's Inc., Wilmington, DE.
[4]Span 80 and Span 20 are tradenames of Sorbitan esters sold by ICI Americas Inc., Wilmington, DE.
[5]E-14-5 ethoxylated amine is the tradename of an ethoxylated amine sold by Exxon Chemical Company, Houston, TX.

EXAMPLES 11–12

In these two examples, Formulations 1 and 2 of Table 1 were prepared and tested in the biodegradation of refinery soil. The N:P ratio of the formulations were 10:1.

The tests were conducted as follows. A refinery soil having weathered hydrocarbon contaminants was used a two week incubation period was allowed. The results of these tests are shown in Table 3.

Additionally, one pan, a control pan, containing untreated soil was watered, hand tilled and subjected to the same tests outlined above. In this instance the control is labeled Comparative Example 1 and the results for it are also given in Table 3.

TABLE 3

| Example | Formulation | % Hydrocarbon Biodegraded In 8 Weeks | Microbial Population MPN Heterotrophs |
|---|---|---|---|
| 11 | 1 | 22 | 7.5 E + 04 |
| 12 | 2 | 20 | 8.6 E + 04 |
| Comparative 1 | — | 2 | 1.7 E + 02 |

The formulations 1–3 listed in Table 1 were also tested using a refinery landfarm soil sludge. In these tests, three kilograms of a refinery landfarm sludge sieved to contain soil particles less than 2 mm in size was added to an oily refinery sludge so that the effective hydrocarbon contaminate on the soil was 2.5 wt. %.

Five polypropylene pans with the same dimensions as outlined in Examples 11 to 12, each containing 3 kilograms of soil were set up and treated with the formulations as shown in the Table 4. To three of the pans the solid formulations were broadcast onto the surface with periodic tilling and mixing of the soil sludge.

The fourth pan was treated with granular urea and sodium phosphate (combined to provide a C:N:P ratio of 100:10:1.) This is labeled Comparative Example 2. In Table 4, the fifth pan was untreated but otherwise watered, hand tilled and tested. The result of the control pan labeled Comparative Example 3 in Table 4.

As indicated, all the pans were watered and tilled three times per week. The percent hydrocarbon that biodegraded was determined by the modified by the EPA 418.1 Test Method outlined above for each pan every two weeks for 9 weeks. From the time versus percent biodegraded data pseudo first order rate constants were determined for each treatment. These results are presented in Table 4.

TABLE 4

| Example | Formulation | % Hydrocarbon Degraded in 9 Weeks | Pseudo First Order Rate Constant (1/days) |
|---|---|---|---|
| 13 | 1 | 18 | 1.14 E − 03 |
| 14 | 2 | 17 | 2.33 E − 03 |
| 15 | 3 | 31 | 4.21 E − 03 |
| Comparative 2 | — | 7 | 4.21 E − 05 |
| Comparative 3 | — | 0 | — |

It should be readily appreciated that the foregoing Examples are not intended to be limiting but merely intended to be illustrative of the mechanisms and materials pertaining to the invention.

What's claimed is:

1. A method for enhancing the biodegradation of hydrocarbon contaminated soil, water and/or sludge comprising applying to the soil, water and/or sludge a degradation effective amount of a composition consisting essentially of a phosphorous source and at least one urea- non-ionic surfactant adduct, wherein the urea and non-ionic surfactant in the adduct are present in a weight ratio ranging from about 98:2 to about 75:25; and wherein the composition has a N:P ratio ranging from about 10:2 to about 10:0.5; and said applying of said composition is carried out to provide in the soil, water, and/or sludge a C:N:P ratio of about 100: 10:1 to about 100:1:001 based on the weight percent of hydrocarbon contaminate in the soil, water and/or sludge.

2. The method of claim 1 wherein the nonionic surfactant of the adduct is selected from the group consisting of alkyl ethoxylates, alkylethoxylated phosphates, alkylethoxylated amines, alkylethoxylated ammonium salts, alkylethoxylated sugars and alkylethoxylated polyhydric alcohols and their cyclic ethers.

3. The method of claim 2 wherein the alkyl group of said non-ionic surfactant has from about 8 to about 22 carbon atoms.

4. The method of claim 3 wherein the surfactant has from about 2 to about 50 ethylene oxide groups.

* * * * *